United States Patent [19]
Carmichael et al.

[11] Patent Number: 5,266,929
[45] Date of Patent: Nov. 30, 1993

[54] METAL CUTTING TOOL WEAR INDICATOR METHOD AND SYSTEM

[75] Inventors: Jerry H. Carmichael, West Chester; Edward N. Diei, Cincinnati, both of Ohio

[73] Assignee: General Electric Company, Cincinnati, Ohio

[21] Appl. No.: 888,065

[22] Filed: May 26, 1992

[51] Int. Cl.⁵ .............................................. G08B 21/00
[52] U.S. Cl. ..................... 340/680; 73/104; 73/660; 364/551.02
[58] Field of Search ................... 340/680; 364/551.02; 73/104, 660

[56] References Cited

U.S. PATENT DOCUMENTS

| | | | |
|---|---|---|---|
| 3,548,648 | 12/1970 | Weichbrodt et al. | 73/104 |
| 4,120,196 | 10/1978 | Hamilton et al. | 73/104 |
| 4,220,995 | 9/1980 | Shoda | 364/508 |
| 4,558,311 | 12/1985 | Forsgren et al. | 340/680 |
| 4,615,216 | 10/1986 | Vykoupil | 73/593 |
| 4,636,779 | 1/1987 | Thomas et al. | 340/680 |
| 4,636,780 | 1/1987 | Thomas et al. | 340/680 |
| 4,642,617 | 2/1987 | Thomas et al. | 340/680 |
| 4,744,242 | 5/1988 | Anderson et al. | 73/104 |
| 4,831,365 | 5/1989 | Thomas et al. | 340/680 |
| 4,918,427 | 4/1990 | Thomas et al. | 340/680 |
| 4,989,159 | 1/1991 | Liszka et al. | 73/660 |

*Primary Examiner*—Glen R. Swann, III
*Attorney, Agent, or Firm*—Jerome C. Squillaro; Charles L. Moore, Jr.

[57] ABSTRACT

In a metal cutting tool wear indicator system, a ratio of an estimated ultrasonic emission signal from a metal cutting process to a measured ultrasonic emission signal, e.g. $\widehat{UE}/\overline{UE}$ is utilized in place of a prior ratio of horsepower to ultrasonic emission, e.g. HP/UE, together with a continuous revision of the estimator during the cutting process.

10 Claims, 1 Drawing Sheet

METAL CUTTING TOOL WEAR INDICATOR METHOD AND SYSTEM

BACKGROUND OF THE INVENTION

This invention relates to a metal cutting tool wear indicator method and system, and more particularly to an improved cutting tool electrical signal analyzing system or process which accurately indicates progression of cutting tool wear for a timely change or intervention into the cutting process. The electrical signal components are selected and processed in such a manner that the usual sensitivities to operating characteristics or cutting conditions which vary from one machine to another are substantially minimized.

Sharp metal cutting tools such as drills, end mills, etc. have significantly different cutting process characteristics than those of dull or worn tools. For example, as a cutting tool wears, more surface area of the tool comes into contact with the workpiece. This increase in surface contact requires an increase in energy input or driving power to the tool as a reaction to a decreasing cutting efficiency. An appropriate power input monitoring system may correlate the increase in power demand for the cutting process with wear of the cutting tool and provide an appropriate signal when a predetermined power demand level is reached. However, if the monitoring system utilizes an electrical signal, a component of which is generated by the cutting tool during its cutting process, the signal may be significantly affected by changes in machine conditions such as tool type, cutter type and composition, tool feed and speed, etc. An advantageous monitoring system is one which more effectively distinguishes a tool wear signal from other machine condition signals.

OBJECTS OF THE INVENTION

Accordingly, it is an object of this invention to provide a metal cutting tool wear indicator system which more effectively establishes and isolates a tool wearing signal from other interfering signals.

It is another object of this invention to provide an improved metal cutting tool wear indicating system which combines an estimated tool generated ultrasonic emission signal and a measured ultrasonic emission for tool wear analysis.

It is still another object of this invention to provide a metal cutting tool wear monitoring system utilizing a continuously revised ratio of an estimated ultrasonic energy signal from a predetermined cutting process to a measured ultrasonic energy signal to determine significant tool wear and provide an appropriate tool wear signal.

SUMMARY OF THE INVENTION

Metal cutting tool wear monitoring systems have utilized hp, horsepower, and ue, ultrasonic emission, signals derived from a metal cutting tool during its cutting process in a ratio of hp/ue which is monitored to determine tool wear. This invention replaces the hp/ue ratio with a different ratio of an estimated ue (related to the cutting process) to a measured ue, i.e. $\widehat{ue}/\overline{ue}$ where $\widehat{ue}$ is derived from a continuously revised quadratic function of hp. The different ratio more readily adapts to a machining or production environment and automatically corrects for part-to-part and machine-to-machine differences.

The following symbols and their definitions are employed throughout this specification and appended claims:

HP—horsepower
UE—ultrasonic emission
hp—horsepower
$\overline{hp}$—mean horsepower
ue—ultrasonic emission
$\overline{ue}$—average or mean ultrasonic emission (measured)
$\widehat{ue}$—estimated average or mean ue
$\widehat{\phantom{x}}$—estimated This invention will be better understood when taken in connection with the following drawings and description.

DESCRIPTION OF A PREFERRED EMBODIMENT

U.S. Pat. No. 4,831,365—Thomas et al May 16, 1989 assigned to the same assignee as the present invention, discloses and describes a metal cutting tool wear detection method which comprises monitoring the ratio of appropriate horsepower and ultrasonic emission signals from the cutting process, i.e. HP/UE. The monitoring system of the present invention utilizes a different but related ratio of an estimated UE to a measured UE where the estimated UE is taken from a quadratic function of HP. These signals are processed by a system best described with respect to FIG. 1.

Figure 1:
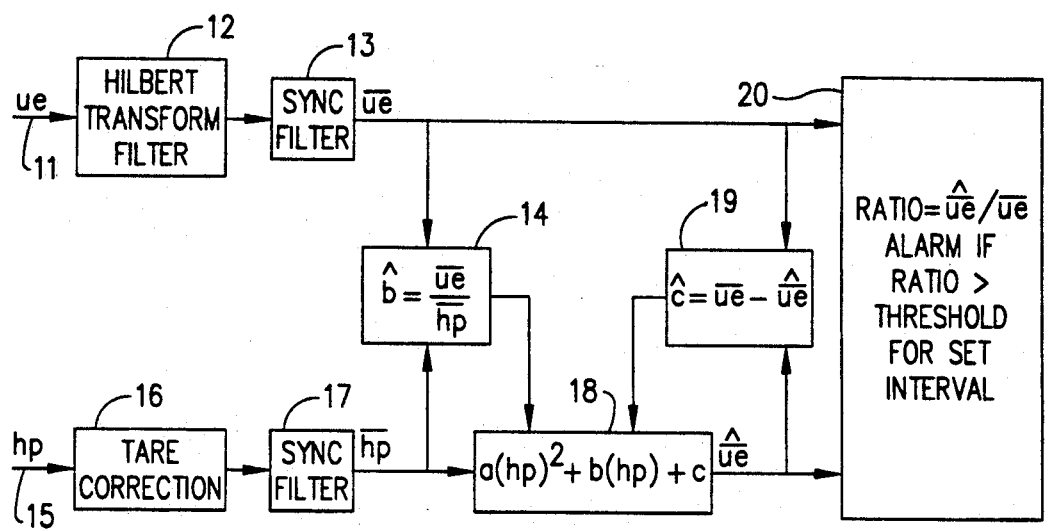
FIG. 1 is a block diagram of a signal processing system utilized to carry on a practice of this invention.

Referring now to FIG. 1, a dual path or channel processing system processes an ultrasonic emission signal (ue) and a horsepower (hp) signal through separate electronic processing paths to provide a ratio of an estimated average ue to a measured ue, a ratio shown in processor 20 of FIG. 1 as $\widehat{ue}/\overline{ue}$. This ratio serves as a basis for a tool wear signal. The ue signal is taken from a cutting tool cutting process by, for example, a wide band accelerometer suitably attached to a cutting tool machine such as on a spindle in which a rotary cutting tool is mounted or on the workpiece or its fixture. The estimated average ue, $\widehat{ue}$, is obtained from the use of a quadratic function of hp. In this invention a quadratic function model was developed from statistical and empirical data from a representative number of related and satisfactory metal cutting operations and is represented by $a(hp)^2 + b(hp) + c$ wherein coefficients b and c are being continuously revised during a cutting process. The coefficient —a— is pre-set for a predetermined general cutting process but is also derived from a representative number of related cutting processes or operations. Such a quadratic function derivation from statistical analysis is a known and accepted practice. The coefficients —b— and —c— of the quadratic function are dynamically revised to provide a continuous modification of the system model as illustrated in the flow diagram of FIG. 1. The coefficients and will be a function of their respective last values plus a percentage of their respective estimated values, b and c.

Referring again to FIG. 1, a ue signal 11 from a wide band accelerometer as described, is passed to a Hilbert Transform filter 12 which serves to correct signal 11, for example, for any extraneous signal component such as spikes caused by breaking and entanglement of metal chips. The output signal from filter 12 is passed to a first synchronous filter 13 which functions to provide a mean average ue signal, $\overline{ue}$, that is corrected for rotational variances of the tool. The output signal from synchronous filter 13 is branched with a branch passing to a coefficient calculator 14 which also receives a mean average hp signal, $\overline{hp}$, from the other of the dual paths of FIG. 1. For example, in the other path of FIG. 1, a suitable horsepower signal 15 is taken from the machine tool cutting process, for example, by monitoring the power input to the tool. Such monitoring may include an induction coil pickup adjacent to an electrical cable providing current to a tool drive motor. The pickup coil will provide an electrical signal indicative of the electrical current taken by the motor and is correlated to horsepower or energy consumed. Signal 15 is passed into a Tare correction filter 16 which removes that part of input signal 15 which is correlated to the energy required to rotate a tool without engaging a workpiece. The corrected output signal from filter 16 is passed to a second synchronous filter 17. Filter 17 provides a mean of its signal averaged over complete multiples of tool spindle revolution. First and second filters 13 and 17 are matched filters. The mean average hp signal, $\overline{hp}$, from filter 17 is branched with a branch passing to coefficient calculator 14. Calculator 14 interconnects matched filters 13 and 17 to continuously calculate an estimted coefficient b, b, the ratio $\overline{ue}/\overline{hp}$. The output signal from coefficient calculator 14 is passed to a ue estimator processor 18 together with a branch signal from synchronous filter 17. Estimator 18 processes a quadratic function, as indicated, and utilizes the input signal from coefficient calculator 14 as well as the hp output signal from synchronous filter 17 to provide an estimated mean average ue, $\underline{ue}$. The estimated mean average ue signal $\underline{ue}$ from estimator 18 is branched with a branch passing to a further calculator 19 along with a branch of the $\overline{ue}$ signal from synchronous filter 13. Calculator 19 calculates an estimated coefficient c, ĉ, for the quadratic function indicated in processor block 18. Coefficient calculator 19 interconnects the two processing channels of FIG. 1 as well as the output signals from synchronous filter 13 and ue estimator 18. Calculator 19 continuously calculates the value of the coefficient —c— of the quadratic function and passes its output signal to processor 18. Processor 18 utilizes the noted quadratic function to provide an estimated mean average ue signal $\underline{ue}$ which is then passed to an adjustable ratio processor 20. Processor 20 determines the ratio of the estimated mean average ue, $\underline{ue}$, to the mean average ue, $\overline{ue}$, from first synchronous filter 13, $\underline{ue}/\overline{ue}$. Also, adjustable ratio processor 20 is equipped with an appropriate audiovisual system which will provide an appropriate audio visual alarm or other signal when conditions indicate excessive tool wear. Ratio processor 20 further includes means to adjust the occurrence of an alarm signal in a time related manner so that the predetermined ratio value which would ordinarily activate an alarm must persist over a predetermined and adjustable time interval for alarm activation. Such adjustability prevents premature alarm signals from spurious conditions and provides better adaptability of the system of this invention to different cutting operations.

The practice of the system of this invention provides a significantly improved metal cutting tool wear indicator system compared to a noted prior system which employs the hp/ue ratio as the base signal. A comparison of results of the two systems is illustrated in FIG. 2.

Figure 2:
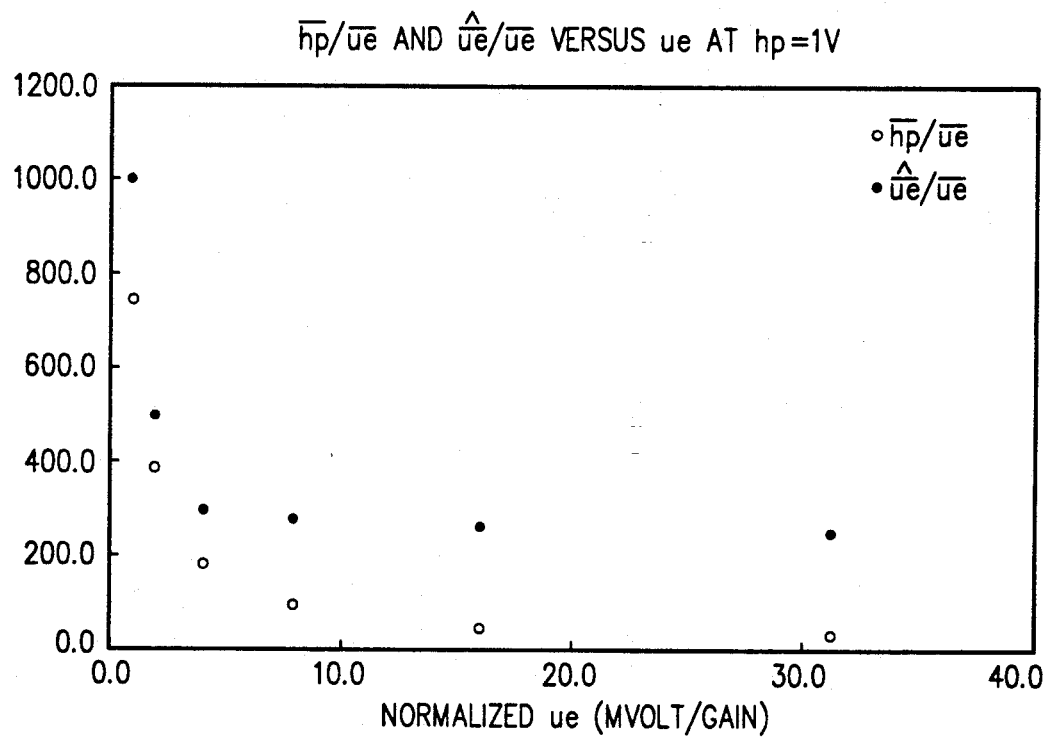
FIG. 2 is a graphical illustration of a comparison of a result of the practice of this invention with a prior HP/UE practice.

Referring now to FIG. 2 the coordinates illustrate the point plots o of a $\overline{hp}/\overline{ue}$ signal which indicates tool wear, together a superimposed point plot ● of a ratio signal, $\underline{ue}/\overline{ue}$ from a practice of this invention. HP was fixed at 1.0 volt and ue was varied over a typical production range of known conditions. The $\overline{hp}/\overline{ue}$ ratio is seen to increase continuously over the ue range while the $\underline{ue}/\overline{ue}$ ratio remains relatively close until a critical region is reached, high $\overline{hp}$ and low $\overline{ue}$, a condition associated with high tool wear. At this region the $\underline{ue}/\overline{ue}$ curve breaks sharply with increasingly spaced points, a clear and early indication of deleterious tool wear. Accordingly, a significant advantage is apparent in that the adjustable ratio processor 20 of FIG. 1 may be adjustably positioned at some ratio threshold level above a usual conservative value to accommodate different cutting conditions.

This invention provides an improved metal cutting tool wear indicating system with a more advantageous and adjustable tool wear threshold ratio. The system disclosed utilizes a continuous revision of its model by means of calculators 14 and 19 which continuously revises the quadratic function coefficients —b— and —c— for automatic adaptability to machine changes.

The combination of an estimation of the expected ue from a cutting process with the use of a Hilbert transform in the averaging process together with the continuous revision or dynamic modification of the quadratic parameters defining the hp and ue relationships provide a significant improvement in the sensitivity of the UE_EST/UE ratio as indicative of tool wear.

While this invention has been disclosed and described with respect to a preferred embodiment, it will be understood by those skilled in the art that various changes and modifications may be made therein without departing from the spirit and scope of this invention.

What is claimed:

1. A method of determining metal cutting tool wear in a metal cutting process comprising
   (a) deriving an ultrasonic emission electrical signal, ue, from said cutting process,
   (b) processing said ue signal to derive a mean average signal, $\overline{ue}$, therefrom,
   (c) deriving a horsepower electrical signal, hp, from said cutting process,
   (d) processing said hp signal to derive a mean average hp signal, $\overline{hp}$, therefrom,
   (e) programming an electrical signal processing calculator to calculate a quadratic function of said hp to determine an estimated mean average of said ue signal, $\underline{ue}$, for said cutting process,
   (f) processing said $\overline{ue}$ and $\underline{ue}$ signals in an adjustable ratio processor to determine a $\underline{ue}/\overline{ue}$ value correlated to cutting tool wear.

2. The invention as recited in claim 1 wherein said adjustable ratio processor includes signal generating means activated when said ratio reaches a predetermined and time related value.

3. The invention as recited in claim 1 wherein said $\overline{ue}$ signal is derived from a ue signal processed through a separate processing path comprising a Hilbert transform filter to remove spikes and through one of a pair of matched synchronous filters to provide a mean average ue signal, $\overline{ue}$, corrected for rotational variance.

4. The invention as recited in claim 3 wherein said hp signal is derived from an hp signal passed through a separate process path comprising a Tare filter and the other of said matched synchronous filters to provide a mean average hp signal, $\overline{hp}$.

5. A method of determining metal cutting tool wear comprising
   (a) deriving an electrical hp signal from said cutting tool representative of the horsepower being applied to said tool during its metal cutting process,
   (b) deriving an electrical ue signal from said cutting tool corresponding to the ultrasonic emission from said tool--during its metal cutting process;
   (c) passing said ue signal through a processing path having electrical signal components including one of a matched pair of synchronous filters which provide a mean average ue signal, $\overline{ue}$, for said process,
   (d) passing said hp signal through a separate processing path having electrical signal processing components therein including the other one of said matched pair of synchronous filters to provide a mean average hp signal, $\overline{hp}$,
   (e) passing said $\overline{hp}$ signal into a quadratic function processor and ue estimator correlated to the quadratic function $a(hp)^2 + b(hp) + c$ to determine an estimated mean average ue, $\overline{ue}$, as an output signal,
   (f) passing said $\overline{hp}$ signal and said $\overline{ue}$ signal into a coefficient calculator to determine the quadratic coefficient b as an estimated b, $\hat{b}$, from the ratio ue/hp,
   (g) continuously passing said estimated coefficient signal to said quadratic function and ue estimator to continuously calculate said estimated mean average ue, $\overline{ue}$, for the cutting process,
   (h) passing said $\overline{ue}$ signal and said $\overline{ue}$ signal to a further coefficient calculator to determine the quadratic coefficient $c$ as an estimated c, $\hat{c}$, from the expression $c = \overline{ue} - \overline{ue}$, said $\hat{c}$ being an input signal to said quadratic function processor and ue estimator,
   (i) passing said $\overline{ue}$ signal and said $\overline{ue}$ signal into an adjustable ratio processor to determine a ratio value from the ratio $\overline{ue}/\overline{ue}$ which indicates tool wear.

6. The invention as recited in claim 5 wherein said further coefficient c calculator interconnects said paths to receive said $\overline{ue}$ signal from one of said synchronous filters and said $\overline{ue}$ signal from said quadratic function processor and ue estimator.

7. The invention as recited in claim 5 wherein said coefficient —b— calculator interconnects said separate paths and said matched pair of synchronous filters to continuously provide a calculated ratio of $\overline{ue}/\overline{hp}$ as the —b— coefficient of said quadratic function.

8. The invention as recited in claim 5 wherein a quadratic coefficient calculator interconnects said one synchronous filter and said quadratic estimator and their output signals to continuously determine the difference between the mean average ue and estimated average ue as the coefficient —c— of said quadratic function.

9. The invention as recited in claim 5 wherein said coefficient calculators are adapted to continuously revise said coefficients during a metal cutting process.

10. The invention as recited in claim 5 wherein said adjustable ratio processor incorporates tool wear signal means with an adjustable time interval for said signal means so that said tool wear ratio value may be time adjusted to persist for a predetermined period of time to activate said signal means.

* * * * *